United States Patent [19]
Lee et al.

[11] Patent Number: 5,284,569
[45] Date of Patent: Feb. 8, 1994

[54] MINIATURE GAS SENSOR

[75] Inventors: Tony C. Lee, Syracuse; Thomas A. Schmitkons, Baldwinsville, both of N.Y.

[73] Assignee: Leybold Inficon Inc., East Syracuse, N.Y.

[21] Appl. No.: 781,079

[22] Filed: Oct. 21, 1991

Related U.S. Application Data

[63] Continuation-in-part of Ser. No. 600,481, Oct. 18, 1990, Pat. No. 5,104,513.

[51] Int. Cl.$^5$ .......................................... G01N 27/407
[52] U.S. Cl. .................... 204/425; 73/31.05; 204/153.13; 204/426; 204/431
[58] Field of Search ............... 204/431, 425, 426, 424, 204/153.13; 73/31.05; 422/98

[56] References Cited

U.S. PATENT DOCUMENTS

| | | | |
|---|---|---|---|
| 3,751,968 | 8/1973 | Loh et al. | 73/31.05 |
| 3,979,625 | 9/1976 | Roberts | 313/230 |
| 3,991,360 | 11/1976 | Orth et al. | 324/468 |
| 4,129,418 | 12/1978 | Davis | 422/98 |
| 4,171,341 | 10/1979 | Morgan | 422/98 |
| 4,470,882 | 9/1984 | Katsura et al. | 204/153.13 |
| 5,104,513 | 4/1992 | Lee et al. | 204/425 |

Primary Examiner—John Niebling
Assistant Examiner—William T. Leader
Attorney, Agent, or Firm—Harris Beach & Wilcox

[57] ABSTRACT

A miniaturized, portable sensor is provided for selectively sensing the presence of halogenated gases, particularly HFC's, within an atmosphere. The apparatus includes a ceramic element containing either a mixture of potassium silicate and either aluminum oxide or silicon dioxide which react with ions of the halogenated gas when the two are brought together forming a depletion layer on and within the ceramic. The sensor is formed with two electrodes on opposite sides of the ceramic having terminals connected into a circuit for detecting a potential difference across the depletion layer. Means are provided for detecting the potential differences and for producing a discernable signal in response thereto.

9 Claims, 1 Drawing Sheet

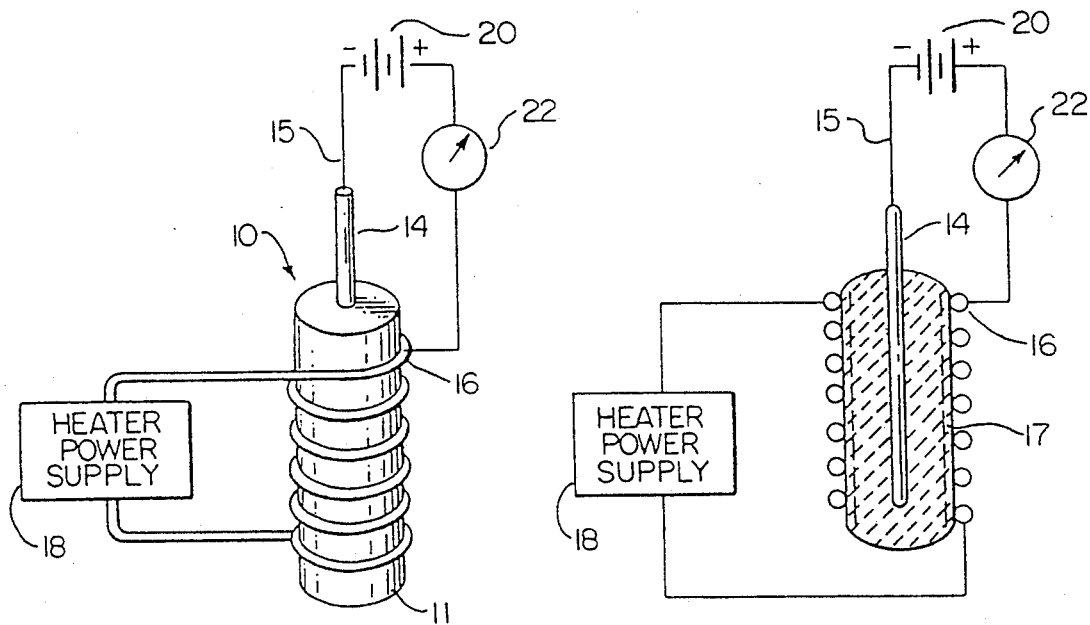

MINIATURE GAS SENSOR

This Application is a continuation-in-part of U.S. Pat. Application No. 600,481, Filed Oct. 18, 1990, now U.S. Pat. No. 5,104,513 for GAS SENSOR.

BACKGROUND OF THE INVENTION

This invention relates to an improved miniaturized solid state sensing device for selectively detecting the presence of gases within an atmosphere, particularly refrigerant gases such as hydro- fluorocarbons (HFC's) and sulphur hexafluoride.

There are many instances where it is necessary to detect the presence of specific gases or vapors in an atmosphere. The gas or vapor may be harmful to human health and thus it may be desirable to monitor a work environment to insure that the concentration of the gas or vapor does not exceed some threshold level. Or, it may be desirable to test pressurized equipment for leaks which could indicate a malfunction. Particular types of gases or vapors which it is desirable to be able to detect are halogen containing gases such as those used as refrigerants and fire extinguishants. For proper operation, leaks from refrigeration, air conditioning, and fire extinguishing equipment must be eliminated or kept to a minimum. Thus, it is necessary to test both components and final assemblies for leaks.

The widely used chlorofluorocarbon (CFC) refrigerants R-12 and R-11 and the fire extinguishants HALON 1301 and HALON 1211 are among the group of chlorinated and/or brominated compounds being phased out or severely restricted by international agreement due to their potential for destroying ozone in the upper atmosphere. The substitutes for these materials in most applications are either hydrofluorocarbons (HFC's) which have no ozone depletion potential or hydrochlorofluorocarbons (HCFC's) which have a significantly reduced ozone depletion potential. For example, the HFC, R-134a (1,1,1,2-tetrafluoroethane), is replacing R-12 (dichlorodifluoromethane) in refrigeration and air conditioning applications where stringent leak testing is required to insure adequate performance of the equipment. Suitable means for detecting leaks is a critical factor in the conversion of this industry to non-ozone depleting chemicals. Although present state of the art gas sensors are quite effective for detecting chlorinated and brominated gases (CFC's, HCFC's, and HALONS), they are not adequate for detecting HFC's.

The prior art of sensors for detecting gases or vapors in an atmosphere has utilized a number of different detection principles. These include 1) measuring changes in the rate of heat loss from a circuit component resulting from changes in thermal conductivity of the atmosphere being sampled 2) electron capture methods which measure ions formed by the gas of interest when it is exposed to low energy electrons 3) positive ion emission methods in which the gas of interest facilitates emission of positive ions from a metal surface in the presence of a strong electric field, and 4) depletion layer methods in which the gas of interest alters the concentration of charge carrying species in a surface depletion layer and thus changes the internal resistance of the sensor.

These prior art sensors all have problems in regard to detection of HFC's. Thermal conductivity detectors are not specific to a given gas and thus are likely to give false responses. They also do not have as high a sensitivity as other types of detectors. Electron capture detectors use a radioactive source which requires special handling and in most cases must be licensed by governmental authorities. Prior art positive ion emission and surface depletion layer detectors have very low sensitivity to HFC's. One way to increase their sensitivity to HFC's is to increase the sensor operating temperature. However, this has the adverse effects of significantly shortening the life of the sensor and greatly increasing its sensitivity to other gases, particularly to chlorinated and/or brominated gases. This extreme sensitivity to minor impurities in the background atmosphere makes existing sensors unsuitable for detecting HFC's.

A solid state sensor having the ability of detecting the presence of many undesirable gases and vapors within an atmosphere is disclosed by Loh in U.S. Pat. No. 3,751,968. A solid state element, which contains alkali metal ions which readily accept negative ions of the subject gases and vapors, is brought into reactive contact therewith. The element is specially prepared to create an outer layer along its boundaries that is depleted of ions. The conductivity of the heated element in an atmosphere free of the reactive gases and vapors is low. However, the presence of one or more of the reactive gases and vapors causes ions to flow across the depletion boundary and increases the conductivity of the element. Electrical circuit means are provided for detecting an increase in the conductivity of the element and generating a signal indicative of the presence of a reactive constituent in the test atmosphere.

The Loh type device has proven to be an extremely useful tool for sensing the presence or absence of a halogen gas within a specific atmosphere. Special applications include leak detection in refrigeration equipment and the presence of potentially dangerous gases within an operating room or the like.

However, many test atmospheres contain more than one constituent that can react with the sensing element and, as a result, unwanted interference signals are sometimes generated that make it difficult to discern the presence of a single gas or vapor of immediate interest. Water vapor, which is ordinarily present in air, has the ability to trigger the sensor and has proven to be troublesome when air sampling is required. Hydrocarbons and chlorine atom containing cleaning solvents such as trichloroethylene have proven to be troublesome background gases commonly found in industrial environments. Because most prior art sensors have low sensitivity to gases which do not contain chlorine or bromine atoms, such as HFC's or sulfur hexafluoride, it has been almost impossible to detect the presence of these gases, particularly when interfering gases are present. The device is conventionally operated within the range of between 700° C. and 850° C. Increasing the sensor operating temperature increases the signal due to gases such as HFC's or sulfur hexafluoride, but also amplifies the unwanted interference signals thus negating any potential benefit. Increased operating temperature also significantly reduces the useful lifetime of the sensor.

In many leak detection applications, small, highly portable leak detection equipment is desirable. As an example, refrigeration and air conditioning service and repair industry workers routinely move leak detectors from site to site. Ideally the leak detector should be a light weight, battery powered device. Most portable refrigeration leak detectors in the prior art operate on the principle of suppression of a corona discharge. These devices are in wide use, but are not as sensitive as heated element type sensors. Of particular importance is their low sensitivity to HFC refrigerants. The prior art heated element sensors also have poor sensitivity to HFC refrigerants, and are generally unsuited to portable operation because they require too much power to be conveniently run by batteries. One exception is the low power positive ion emission device which is disclosed in U.S. Pat. No. 3,979,625 to Roberts. This patent explains the technical difficulties encountered in constructing a miniaturized version of the heated element sensor. The same difficulties are encountered in miniaturizing heated elements sensors which operate on the depletion layer principle. Although this type of sensor has a glass-ceramic layer separating the electrode, there is a tendency, espcially in small sensors, for electrical shorts to develop during extended operation at high temperatures. This problem is particularly severe in the case of HFC detectors, since higher operating temperatures are required to increase sensitivity to these compounds.

SUMMARY OF THE INVENTION

It is therefore a primary object of the present invention to provide an improved sensor for detecting halogen containing gases which operates at a low power consumption.

It is another object of the present invention to provide a light-weight, portable sensor for detecting halogen containing gases which can be powered by batteries.

It is a further object of the present invention to provide a low power sensor which is sensitive not only to chlorine and bromine containing halocarbons, but also to gases in which fluorine is the only halogen, such as HFC's and sulfur hexafluoride.

A still further object of the present invention is to provide an improved miniaturized detector for halogen containing gases which has enough selectivity to detect fluorine containing gases in the presence of low levels of chlorinated or brominated gas impurities.

These and other objects of the present invention are attained by a miniature gas detector that operates on the depletion layer principle and has a novel ceramic composition. The device has a useful operating temperature range for detecting HFC's in excess of 750° C.

BRIEF DESCRIPTION OF THE DRAWINGS

For a better understanding of these and other objects of the present invention, reference is made to the detailed description of the invention which is to be read in conjunction with the following drawings, wherein:

FIG. 1 is a perspective view of a sensor embodying the teachings of the invention shown connected in a schematically illustrated circuit;

FIG. 2 is an enlarged longitudinal cross-sectional view through the sensor as shown in FIG. 1.

DETAILED DESCRIPTION OF THE INVENTION

Referring now more particularly to FIGS. 1 and 2 of the drawings, a sensor, shown generally at 10, is formed in a symmetrical configuration. This illustrated preferred embodiment is shown intended for the sensing of halogen containing gases, in which case the sensing element 11 is formed of a glass ceramic material. In the present invention, the ceramic is preferably composed of a mixture of an potassium silicate and oxides of aluminum and/or silicon. The ceramic forms an electrically resistive layer between a cathode 14 and an anode 16. The electrodes can be platinum, palladium, alloys of platinum or palladium, or other metals which can survive the high operating temperature. The most preferred composition is a mixture of potassium silicate and aluminum oxide. A variety of weight ratios may be used. A weight ratio of one part aluminum oxide by weight to between about 0.25 and 4.0 parts potassium silicate by weight can be used in the practice of the invention. A preferred ratio is one part aluminum oxide by weight to between about 1.5 and 2.5 parts potassium silicate by weight. The composition of the potassium silicate is not critical and a weight ratio of one part potassium oxide to between about 1.6 and 2.5 parts silicon dioxide may be used. A particularly useful form of potassium silicate has been found to be KASIL (PQ Corporation, Valley Forge, PA) liquid potassium silicate. By way of example, KASIL is a water solution containing 36% by weight solids with a silicon dioxide to potassium oxide weight ratio of 2.1.

Aluminum oxide and silicon dioxide can vary in particle size. The typical average particle size is less than 15 microns. A preferred average particle size is less than 1 micron. The heater coil 16 also serves as an anode. It should be understood by those skilled in the art that a separate conductive element could serve as an anode without departing from the spirit of the invention.

The cathode 14 is a wire having a thickness in the range of 1 to 15 mils, while the anode/heating element 16 is a coil formed from a wire having a thickness in the range of 1 to 5 mils. These dimensions are preferable ranges that are large enough to accomplish the functions desired in the device, yet small enough to minimize power requirements. Other dimensions can be used as dictated by particular applications.

In one embodiment of the invention, a sensor is made by coating a central platinum electrode with a slurry made from potassium silicate and aluminum oxide. When the coating has dried, the coated wire is positioned inside the coils of a platinum wire anode formed into the shape of a cylindrical helix. Additional slurry is applied to fill any gaps between the anode coils and the first layer of slurry and the assembly is then fired. It will be apparent to those skilled in the art that when working with miniature devices as described herein, variations in the application of the slurry such as spray or dip coating can facilitate construction.

The preferred firing temperature is in the range of 600° C. –1,300° C. The firing step may be omitted. However, the length of the subsequent conditioning step necessary to form the depletion layer will be extended. The sensor element may be mounted in a suitable holder with electrically isolated leads which allow electricity to flow to the sensor for activating the heater, applying a bias potential across the electrodes, and monitoring the current passing through the sensor. The sensor is conditioned by passing a current through the anode heater coil sufficient to produce a coil temperature of 600° C.–1,000° C. and simultaneously applying a DC voltage between one lead of the heater coil and the central electrode. A bias voltage of between 0.5 and 5 volts is applied such that the central electrode is held negative with respect to the heater coil. A depletion layer is formed in the ceramic by current passing between the electrodes. The current rapidly decreases during the first few hours of conditioning, but stabilizes within approximately 24 hours, indicating that the depletion layer has formed.

The device is disposed in a small housing suitable for portable, hand-held operation, and the sensor is coupled to conventional miniaturized electronic circuitry as discussed below. It can conveniently be powered by batteries. Thereafter, in operation of the device, an ammeter 22, or similar device responsive to the flow of current between terminals 15 and 16 is arranged in the circuit. The ammeter 22 is illustratively shown in FIG. 1 as arranged in series with the sensor 10 and the biasing voltage power supply 20. If a halogen containing gas is present in the atmosphere adjacent sensor 10, the current passing through the sensing element increases and the increase is indicated by a change in the meter reading.

The sensors disclosed herein can be used to detect CFC's, HCFC'S, and HFC's. The device can detect halogenated gases in which fluorine is not the only halogen when it is operated at temperatures less than about 750°-800° C., and the minimum useful operating temperature for detecting gases such as CFC's and HCFC's is about 600° C. The minimum useful operating temperature for detecting HFC's in the presence of small amounts of CFC's and HCFC's is about 750° C. These sensors have good sensitivity for HFC's, such as R134a, when operated in the temperature range of 750° C. to 950° C., and so far as is known to the inventors, greater sensitivity than sensors made according to the prior art when operated in this temperature range. At temperatures exceeding 950° C., the sensor lifetime is shortened.

EXAMPLE

A helical coil with an inside diameter of approximately 0.020 inches is made from a ⅛ inch of 0.003 inch diameter platinum wire. One end (approximately ⅛ inch) of a length of 5 mil diameter platinum wire is coated with aluminum oxide potassium silicate slurry having a composition of 2.3 parts postassium silicate by weight to 1 part aluminum oxide by weight. The coating is built up in layers, each layer being air dried before the next layer is applied, until the coated wire fits snugly, but easily, inside the helical coil. The coil is positioned over the coated end of the wire and a final, thin layer of slurry is applied over the coil. It is evident that the wire and the coil are now separated by 0.0075 inches. This assembly is air dried for 2 hours and then baked in an oven (ramped to 850° C. at 100 degrees per hour, then held at 850° C. for one hour). It is then mounted to appropriate electrical leads in an appropriate housing. A current is passed through the coil to heat the sensor to approximately 800° C. while the center electrode is biased at approximately −2.0 volts with respect to the ground side of the heated coil. The sensor is aged in this way for about 5 hours in order to establish the depletion layer.

A sensor built according to this example and attached to appropriate electronic detection circuitry is able to detect leaks of R134a of less than 0.1 ounces per year.

While this invention has been explained with reference to the structure disclosed herein, it is not confined to the details set forth and this application is intended to cover any modifications and changes as may come within the scope of the following claims:

We claim:

1. A solid state electrochemical sensor for detecting the presence of a halogenated gas contained within an atmosphere, said device comprising:

an anode, comprising an electrically conductive wire between about 1 mil to 5 mils in diameter;

a cathode, comprising an electrically conductive wire between about 1 mil to 5 mils in diameter;

a ceramic, comprising a mixture of potassium silicate and a compound selected from the group consisting of silicon dioxide and aluminum oxide, interposed between said anode and said cathode and having a depletion layer formed therein, said ceramic being selectively reactive with fluorine containing gas in the presence of a gas containing a halogen other than fluorine when said device is operated at a temperature of at least about 750° C., said anode and said cathode being separated by a distance not exceeding about 0.0075 inches; and heating means for raising the temperature of said ceramic to a desired level.

2. The device of claim 1 wherein said ceramic is reactive with a given halogenated gas when said device is operated at a temperature less than about 750° C.

3. A portable, solid state electrochemical device for detecting the presence of a halogenated gas contained within an atmosphere, said device comprising:

an anode, comprising an electrically conductive wire between about 1 mil to 5 mils in diameter;

a cathode, comprising an electrically conductive wire between about 1 mil to 5 mils in diameter;

a ceramic, comprising a mixture of potassium silicate and a compound selected from the group consisting of silicon dioxide and aluminum oxide, interposed between said anode and said cathode and having a depletion layer formed therein, said ceramic being selectively reactive with fluorine containing gas in the presence of a gas containing a halogen other than fluorine when said device is operated at a temperature of at least about 750° C., said anode being helically coiled about said ceramic and being separated from said cathode by a distance not exceeding about 0.0075 inches;

heating means for raising the temperature of said ceramic to a desired level;

electrical circuit means, connected across said anode and said cathode for holding said cathode negative with respect to said anode;

electrical measurement means connected in said electrical circuit means for providing an indication when said ceramic reacts with a given gas; and electrical power means connected to said heating means.

4. The device of claim 3 wherein said ceramic is reactive with a given halogenated gas when said device is operated at a temperature less than about 750° C.

5. A portable, hand-held solid state electrochemical device for detecting the presence of a halogenated gas contained within an atmosphere, said device comprising:

an anode, comprising an electrically conductive wire between about 1 mil to 5 mils in diameter;

a cathode, comprising an electrically conductive wire between about 1 mil to 5 mils in diameter;

a ceramic, comprising a mixture of potassium silicate and aluminum oxide in a ratio of between about 0.25-4.0 parts potassium silicate by weight to 1 part aluminum oxide by weight, interposed between said anode and said cathode and having a depletion layer formed therein, said ceramic being selectively reactive with fluorine containing as in the presence of a gas containing a halogen other than fluorine when said device is operated at a temperature of at least about 750° C., said anode being helically coiled about said ceramic and being separated from said cathode by a distance that does not exceed about 0.0075 inches;

heating means for raising the temperature of said ceramic to a desired level;

electrical circuit means, connected across said anode and said cathode for holding said cathode negative with respect to said anode;

electrical measurement means connected in said electrical circuit means for providing an indication when said ceramic reacts with a given gas; and electrical power means connected to said heating means.

6. The device of claim 5 wherein said ceramic is reactive with a given halogenated gas when said device is operated at a temperature less than about 750° C.

7. A portable, hand-held solid state electrochemical device for detecting the presence of a halogenated gas contained within an atmosphere, said device comprising:

an anode, comprising an electrically conducive wire between about 1 mil to 5 mils in diameter;

a cathode, comprising an electrically conductive wire between about 1 mil to 5 mils in diameter;

a ceramic, comprising a mixture of potassium silicate and aluminum oxide in a ratio of between about 1.5-2.5 parts potassium silicate by weight to 1part aluminum oxide by weight, interposed between said anode and said cathode and having a depletion layer formed therein, said ceramic being selectively reactive with fluorine containing as in the presence of a gas containing a halogen other than fluorine when said device is operated at a temperature of at least about 750° C., said anode being helically coiled about said ceramic and being separated from said cathode by a distance that does not exceed about 0.0075 inches;

heating means for raising the temperature of said ceramic to a desired level;

electrical circuit means, connected across said anode and said cathode for holding said cathode negative with respect to said anode;

electrical measurement means connected in said electrical circuit means for providing an indication when said ceramic reacts with a given gas; and electrical power means connected to said heating means.

8. The device of claim 7 wherein said ceramic is reactive with a halogenated gas when said device is operated at a temperature less than about 750° C.

9. A solid state electrochemical device for detecting the presence of a halogenated gas contained within an atmosphere, said device comprising:

an anode, comprising an electrically conductive wire between about 1 mil to 5 mils in diameter;

a cathode, comprising an electrically conductive wire between about 1 mil to 5 mils in diameter;

a ceramic, comprising a mixture of potassium silicate and a compound selected from the group consisting of silicon dioxide and aluminum oxide, interposed between said anode and said cathode and having a depletion layer formed therein, said ceramic being reactive with a gas containing a halogen other than fluorine when said device is operated at a temperature of less than about 750° C., said anode being helically coiled about said ceramic and being separated from said cathode by a distance that does not exceed about 0.0075 inches;

heating means for raising the temperature of said ceramic to a desired level;

electrical circuit means, connected across said anode and said cathode for holding said cathode negative with respect to said anode;

electrical measurement means connected in said electrical circuit means for providing an indication when said ceramic reacts with a given gas; and electrical power means connected to said heating means.

* * * * *